United States Patent
Dervieux (10) Patent No.: US 11,338,133 B2
(45) Date of Patent: May 24, 2022

(54) DEVICE FOR RELIEVING PAINS AND SPASMS COMPRISING A DEVICE FOR PROTECTING AGAINST STATIC ELECTRICITY AND A DEVICE FOR TRIGGERING THE ACTIVATION OF SAID RELIEVING DEVICE

(71) Applicant: Dominique Dervieux, Paris (FR)

(72) Inventor: Dominique Dervieux, Paris (FR)

( * ) Notice: Subject to any disclaimer, the term of this patent is extended or adjusted under 35 U.S.C. 154(b) by 179 days.

(21) Appl. No.: 16/058,853

(22) Filed: Aug. 8, 2018

(65) Prior Publication Data

US 2019/0046790 A1   Feb. 14, 2019

(30) Foreign Application Priority Data

Aug. 8, 2017 (FR) ...................................... 1757584

(51) Int. Cl.
| | |
|---|---|
| *A61N 1/10* | (2006.01) |
| *A61N 1/14* | (2006.01) |
| *A61N 1/04* | (2006.01) |
| *A61N 1/36* | (2006.01) |
| *A61N 1/32* | (2006.01) |
| *A61N 1/08* | (2006.01) |

(52) U.S. Cl.
CPC ............ *A61N 1/14* (2013.01); *A61N 1/0456* (2013.01); *A61N 1/0472* (2013.01); *A61N 1/0476* (2013.01); *A61N 1/08* (2013.01); *A61N 1/322* (2013.01); *A61N 1/36003* (2013.01); *A61N 1/36021* (2013.01)

(58) Field of Classification Search
CPC ...... A61N 1/14; A61N 1/0456; A61N 1/0472; A61N 1/08; A61N 1/322; A61N 1/0476; A61N 1/36003; A61N 1/36021
See application file for complete search history.

(56) References Cited

U.S. PATENT DOCUMENTS

| | | | | |
|---|---|---|---|---|
| 2,477,520 A | * | 7/1949 | Mansfield | G01R 31/72 313/49 |
| 4,823,810 A | * | 4/1989 | Dervieux | A61N 1/0472 607/46 |
| 4,920,981 A | * | 5/1990 | Dervieux | A61H 39/002 607/145 |

(Continued)

FOREIGN PATENT DOCUMENTS

| | | |
|---|---|---|
| CN | 103165594 A | 6/2013 |
| FR | 2563735 A1 | 11/1985 |

OTHER PUBLICATIONS

Search Report and Written Opinion dated Apr. 17, 2018 for Application No. FR 1757584.

*Primary Examiner* — Eugene T Wu
(74) *Attorney, Agent, or Firm* — Crowell & Moring LLP (57) ABSTRACT

A device for relieving pains and spasms by applying electrical pulses which makes it possible to render the electrical pulses easier to tolerate by limiting or preventing the painful or untimely discharges which hamper the use of the relief device. The relief device delivers electrical pulses only when it bears or rolls in a back-and-forth movement on the skin or clothing of a user. The relief device comprises means for limiting the maximum voltage delivered to the user, one or more means of triggering the pulses delivered by the electrodes, an activation delayer and a system for progressively launching the potential delivered by the electrodes.

19 Claims, 7 Drawing Sheets

(56) References Cited

U.S. PATENT DOCUMENTS

| | | | |
|---|---|---|---|
| 5,430,604 A * | 7/1995 | Wong | G01R 31/001 324/122 |
| 6,026,327 A * | 2/2000 | Dervieux | A61N 1/322 607/145 |
| 6,873,516 B1 | 3/2005 | Epstein | |
| 10,032,761 B1 * | 7/2018 | Choppalli | H01L 21/0251 |
| 2002/0151200 A1 * | 10/2002 | Fauser | H01T 4/08 439/181 |
| 2002/0161324 A1 | 10/2002 | Henley et al. | |
| 2004/0171970 A1 | 9/2004 | Schleuniger et al. | |
| 2005/0283203 A1 | 12/2005 | Flaherty et al. | |
| 2007/0173909 A1 * | 7/2007 | Inman | A61N 1/14 607/63 |
| 2015/0051685 A1 * | 2/2015 | Schroeder | A61N 1/36021 607/148 |

* cited by examiner

DEVICE FOR RELIEVING PAINS AND SPASMS COMPRISING A DEVICE FOR PROTECTING AGAINST STATIC ELECTRICITY AND A DEVICE FOR TRIGGERING THE ACTIVATION OF SAID RELIEVING DEVICE

CROSS REFERENCE TO RELATED APPLICATIONS

This application claims the benefit of French Patent Application No. 1757584 filed Aug. 8, 2017, which is incorporated by reference herein in its entirety.

FIELD OF THE INVENTION

The present invention relates to the field of relief and comfort and, more specifically, the field of relieving the pains and spasms of everyday life. Thus, the present invention relates to a device for relieving pains and spasms by applying electrical pulses and which, more specifically, comprises at least one protection device for limiting discharges of static electricity when such a relief device is applied onto a user, for example onto the skin, onto a fabric or an item of clothing. The present invention also relates to an activation triggering device in order to enable the relief device to function solely when it is applied or is going to be applied onto the user. Thus, when the relief device is applied onto the user, in particular by following an alternating back-and-forth movement, electrical pulses are generated on the user's skin to relieve spasms or pains. Furthermore, the relief device is configured to protect the user by limiting the generation of discharges of the static electricity which accumulates in the relief device during prior usage and which may potentially discharge while being picked up, while being placed on a part of the body, or during sweeping by an alternating back-and-forth movement of the relief device on an area of the user's body to which relief is to be offered.

PRIOR ART

In the background art, there are various portable devices for relieving pains and spasms by applying electrical pulses, and such devices are described for example in patent application WO9707855. These relief devices are often equipped with a rheostat for adjusting the intensity and may use a "spark gap" or discharger to limit static electricity discharges to a chosen level. However, these relief devices again need to be improved to prevent untimely discharges of static electricity which form electric arcs, when static electricity, which accumulates in the relief device during earlier use, discharges, in particular as a result of the relief device getting close to the user who thus serves as a ground, even through a fabric or a porous element. Thus, such devices are rejected by many users who are of the view that the static electricity discharges felt are too strong, too violent and that the untimely discharges felt are painful. Such discharges are produced for example when the head of the relief device which is intended to be applied onto the user is touched with a finger when static electricity has accumulated during earlier use at the electrodes which are arranged on the electrode head of the relief device. Thus, such discharges may be generated if the activated relief device is applied onto the user before starting to carry out an alternating back-and-forth movement, or even by absence of contact, when the relief device is brought towards the user's skin, which makes its use painful. It has also been observed that simply starting the pulses on the skin suddenly and non-progressively is painful, regardless of the type of the relief device's electrical supply which may be electronic or quartz.

It is currently easy to effectively set the intensity of the power supply current of these relief devices, in particular by mechanical or electronic rheostats. However, it is less easy to set the voltage of the static electricity which may accumulate on the electrodes of these relief devices and discharge suddenly at a voltage which may be higher than the voltage of the pulses delivered to the user during alternating back-and-forth movements on his/her body. Moreover, a correlation has been established between the voltage of the electrical pulses and the distance between the electrodes and a discharge surface, such as a user's skin where electric arcs may be generated and cause pain. Thus, it has been observed that each multiple of 100 volts discharges at a distance of a multiple of one-tenth of a millimeter: an electric arc of 400 volts will thus be triggered at a distance of four-tenths of a millimeter between the electrodes.

These relief devices are frequently rejected by numerous sensitive users from their first use, which leads to these devices being returned to the seller and to said devices having a bad reputation.

It therefore proves to be vital to once again improve these devices for relieving everyday pains and spasms by controlling the application of their electrical pulses in order to make them acceptable to everyone, by limiting the untimely static electricity discharges or at least by limiting the voltage of such discharges to adapt to the sensitivity of the users.

OBJECT OF THE INVENTION

The invention relates to a device for the relief of pains and spasms comprising a housing, an electrode head which supports at least two electrodes intended to be applied on an area of use and which is mounted onto the housing, and an electrical circuit for delivering electrical pulses by means of the electrodes, said relief device being characterized in that it comprises:
  a device for protecting against static electricity discharges which comprises static electricity discharge elements associated in pairs and adjustably spaced apart from one another, and
  an activation triggering device configured to trigger the activation of the electrical circuit when the relief device bears on the area of use.

According to the invention, the relief device enables the delivery of electrical pulses by means of the electrodes only when it is applied onto the area of use and enables an adjustable discharge of static electricity, which provides each user with a comfort of use which is adaptable to his/her sensitivity.

The invention may also comprise the advantageous aspects listed below, alone or in combination:
  the protection device may be arranged in the housing and at least two associated static electricity discharge elements may be placed end-to-end in the electrical circuit to face one another, the spacing between the two associated static electricity discharge elements being adjustable between 0.2 mm and 1 mm. By virtue of this gap that is adjustable between 0.2 mm and 1 mm, the static electricity discharge level may be adapted according to the sensitivity of the user.

the protection device may comprise at least two capacitors arranged in the electrical circuit and configured to discharge static electricity of the relief device at different voltage values.

This also makes it possible to adapt the static electricity discharge level according to the sensitivity of the user.

the protection device may comprise at least two static electricity discharge elements situated outside of the housing and made up of two electrodes, the ends of which are placed end-to-end to face one another, the spacing between the ends of the two electrodes being able to be between 0.2 mm and 1 mm.

The electrodes thus act as a static electricity discharge element which simplifies the design of the relief device's electrical circuit and consequently allows a reduction in the size and mass thereof.

The spacing between the ends of the two electrodes may be adjustable, in particular by screwing an electrode onto the housing. It is thus possible to adapt the static electricity discharge level according to the sensitivity of the user.

the protection device may comprise an adjustment device configured for adjusting a minimum distance between the electrodes and the area of use. This minimum distance makes it possible to protect the user from any discharge of parasitic electricity below a predetermined voltage.

the electrode head may comprise neutral-polarity washers, the electrodes and the neutral-polarity washers being able to be disposed in a cylindrical space delimited by the neutral-polarity washers, each neutral-polarity washer being able to be disposed between two adjacent electrodes of opposite polarity, with the neutral-polarity washers being able to project beyond the electrodes in a radial direction of the cylindrical space delimited by the neutral-polarity washers. This embodiment presents a simply implementable way of limiting parasitic discharges.

the activation triggering device may be configured to trigger the activation of the electrical circuit when at least one neutral-polarity washer is bearing on the area of use, the neutral-polarity washer being able to be preferably arranged in a central part of the cylindrical space.

Thus, the relief device delivers electrical pulses by means of the electrodes only when it is bearing on an area of use.

the activation triggering device is configured to trigger the activation of the electrical circuit when a relative movement occurs between the electrode head and the housing.

The detection of a relative movement between the electrode head and the housing is a way of effectively detecting the bearing of the relief device on an area of use. In particular, such a relative movement may be identified by a detection carried out by a sensor of the laser, ultrasound, or infrared type or by a device for acquiring images such as a camera.

the relative movement between the electrode head and the housing may be a retraction movement of the electrode head into the housing.

Such a retraction movement may be detected by simple means such as pressure, blade or bead mechanical contacts which trigger an activation contact in the electrical circuit to deliver electrical pulses by means of the electrodes, the contact being brought about by the relief device bearing on the area of use.

the activation triggering device may be configured to trigger the activation of the electrical circuit when at least one roller that is included in the electrode head and that is rotationally fixed to a current-generating dynamo rolls on the area of use.

When the roller rolls on the area of use, the dynamo which is rotationally fixed to the roller generates an electrical current, this electrical current is detected by a current detecting electronic system of the activation triggering device, then once this current is detected, the activation triggering device triggers the activation of the electrical circuit. This coupling between a dynamo and at least one roller is a means which may be easily implemented to detect that the relief device bears on and moves on an area of use.

the activation triggering device may be configured to trigger the activation of the electrical circuit when the direction of the application movement of the relief device on the area of use is changed, the application movement being an alternating movement, such as a back-and-forth movement.

The detection of the change of direction of the application movement of the relief device on the area of use may be carried out, for example, by means of a roller coupled with a micro-dynamo or by two cylinders with a bead for contacting two ends, of the cylinders, placed end-to-end, or by the sliding of a cylindrical balancing weight or mercury or by a pendulum system which establishes an electrical contact in the electrical circuit at the two ends of the pendulum movement.

the electrical circuit is connected to an activation electronic system configured to delay the activation and/or progressively increase the potential of the electrical pulses delivered by means of the electrodes, preferably for from half of a second to one second after the activation triggering device triggers the activation of the electrical circuit.

By delaying the activation or by progressively increasing the potential, the user's comfort is improved since he/she receives delayed and/or progressive pulses which are adapted to his/her sensitivity.

the electrical circuit may be connected to an electronic system for controlling activation that is configured to increase the potential of the electrical pulses delivered by means of the electrodes in accordance with the activation frequency of the activation triggering device.

The pulses are thus delivered in a manner adapted to the sensitivity of the user by taking into account the frequency of activation of the activation triggering device.

a piezoelectric quartz may be connected on the one hand to a manually actuated lever and on the other hand to the electrical circuit to deliver the electrical pulses by means of the electrodes, the lever being able to be configured to adjust the potential of the electrical pulses by compression of the lever on the piezoelectric quartz and a dampening device being able to be configured to dampen the compression of the lever on the piezoelectric quartz.

The dampening device in particular makes it possible to limit the compression of the piezoelectric quartz and therefore to limit the maximum voltage of the electrical pulses delivered to the user when a manual pressure is exerted onto the lever to deliver electrical pulses onto the area of use.

a piezoelectric quartz may be connected on the one hand to a connecting rod which cooperates with at least one washer that has an elliptical cross-section and on the other hand to the electrical circuit to deliver the electrical pulses by means of the electrodes, the connecting rod may have a first longitudinal end and a second longitudinal end opposite the first longitudinal end, the first longitudinal end of the connecting rod being able to be engaged with the at least one washer which has an elliptical cross-section and which is rotationally fixed to the neutral-polarity washers, and the second longitudinal end of the connecting rod being configured to follow a back-and-forth movement for compression of the piezoelectric quartz when the neutral-polarity washers are rotated.

When the relief device moves on the area of use, it rolls on the area of use by applying the neutral-polarity washers onto the area of use, the rolling of the neutral-polarity washers rotates at least one integral washer which has an elliptical cross-section, which drives the connecting rod to compress the piezoelectric quartz according to a back-and-forth movement. The compression of the quartz then supplies power to the electrodes to deliver electrical pulses onto the area of use. Such a mechanical coupling between elliptical washers (which form a crank) and a connecting rod makes it possible to integrate the piezoelectric quartz compression system in the relief device to reduce its size and to improve the user's comfort since this coupling allows electrical pulses to be delivered onto the area of use only when the relief device rolls on the area of use.

BRIEF DESCRIPTION OF THE DRAWINGS

The aims, objects and characteristics of the present invention, as well as its advantages, will become more clearly apparent when reading the following description of preferred embodiments with reference to the drawings in which.

DETAILED DESCRIPTION OF THE EMBODIMENTS

The detailed description hereafter aims to explain the invention in a manner that is sufficiently clear and complete, notably with the aid of examples, but must not be considered as limiting the scope of the protection to the specific embodiments and the examples presented hereafter.

The present invention relates to a device for relieving pains and spasms by applying electrical pulses by means of electrodes which are arranged at an electrode head intended to come into contact with an area of use, for example the skin of a user. The relief device comprises a housing, or a body, in which there is arranged an electrical circuit suitable for generating electrical pulses by means of the electrodes. An example of a piezoelectric quartz relief device 100, 110 is illustrated in FIGS. 2a, 2b, 3a, 3b, 3c and 3d. Another example of a relief device 200 without piezoelectric quartz, which is referred to as electrical, is illustrated in FIGS. 4a, 4b, 5a and 5b.

According to several embodiments, the invention relates to various devices for protecting a user against static electricity discharges by limiting the voltage delivered by the static electricity discharges from the relief device 100, 110, 200. The device for protecting against the static electricity discharges from the relief device comprises for example two conducting wires, two plates, two rounded or pointed shapes or other conducting shapes, hollow or solid, placed end-to-end as shown in FIGS. 1a to 1e. These different elements are spaced apart by a few tenths of a millimeter up to several millimeters in order to allow limitation of the voltage of the static electricity discharges. FIGS. 1a to 1e thus respectively illustrate a first, a second, a third, a fourth and a fifth embodiment for such a device for protecting against static electricity discharges, which, alone or in combination, form one or more "spark gaps" arranged for example in the housing of the relief device 100, 110, 200.

Thus, throughout the rest of the description, we will call a device for protecting a user against a static electricity discharge voltage from the relief device a "spark gap".

Figure 1A:
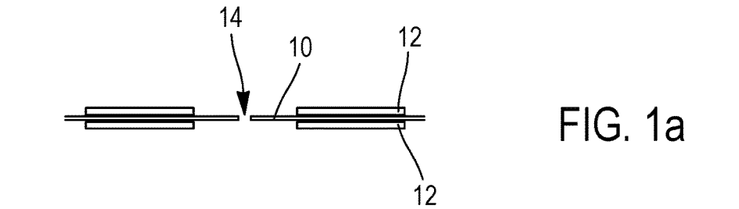
FIG. 1a schematically shows two conducting wires placed end-to-end to enable a discharge of static electricity according to a first embodiment example of the invention, each wire preferably being fixed to a support to keep a gap between them, FIG. 1b schematically shows two conducting plates, which are metal, for example, and which are placed end-to-end to enable a discharge of static electricity according to a second embodiment example of the invention, and each plate may be fixed onto a fixed support to keep a gap between them, FIG. 1c schematically shows two conducting elements according to a third embodiment example of the invention which have a sphere-portion shape or a rounded shape which may be hollow or solid and which are placed end-to-end to enable a discharge of static electricity, each element being able to be fixed to a support in order to keep a gap between them, FIG. 1d schematically shows two points placed end-to-end according to a fourth embodiment example of the invention in order to enable a discharge of static electricity and which may have a cone shape, each of these points or cones being able to be fixed to a support in order to keep a gap between them, FIG. 1e schematically shows a fixed point placed end-to-end with a screw according to a fifth embodiment example of the invention in order to enable a discharge of static electricity, the screw being able to screw onto a support in order to vary the static electricity discharge voltage according to the gap defined between the point and the screw.

More precisely, as illustrated in FIG. 1a, at least two conducting wires 10, for example of copper wire type may be arranged in a protective isolating sleeve 12 or be bare. The wires are spaced apart by a few tenths of a millimeter to a millimeter to form a spark gap. Each wire may be fixed onto a support or onto inner walls of the relief device 100, 200.

Figure 1B:
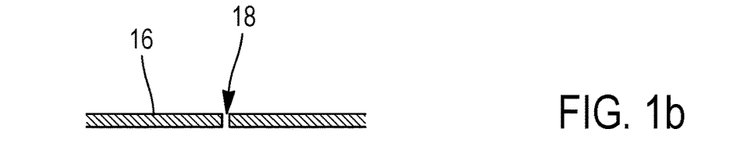

As illustrated in FIG. 1b, at least two metal conducting plates 16 may be placed end-to-end and be spaced apart by a few tenths of a millimeter to one millimeter in order to form a spark gap. Each plate 16 may be fixed onto a support or onto inner walls of the relief device 100, 200. It is thus necessary to place each plate 16 end-to-end, keeping between them a spacing from one to several tenths of a millimeter.

Figure 1C:
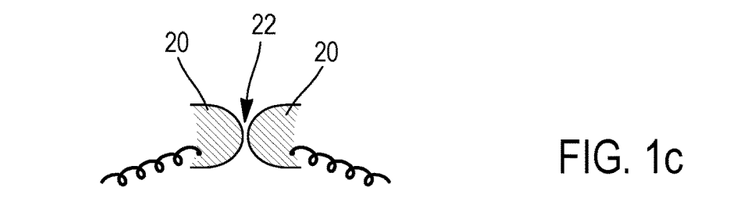

In FIG. 1c, two sphere-portion or rounded shapes 20, hollow or solid, form a spark gap 22. These shapes 20 may be fixed to a support in the relief device 100, 200 in order to keep the gap between them.

Figure 1D:
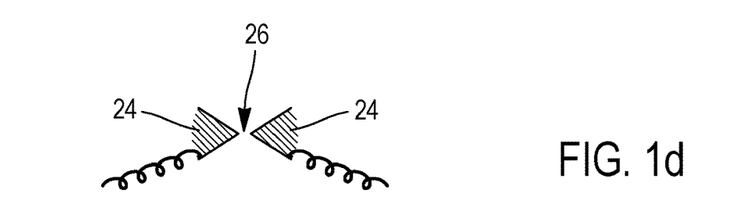

In FIG. 1d, two points 24 or two cones are placed end-to-end in order to form a spark gap 26. The points 24 may be fixed to a support in the relief device 100, 200 in order to keep the gap between them.

Figure 3A:
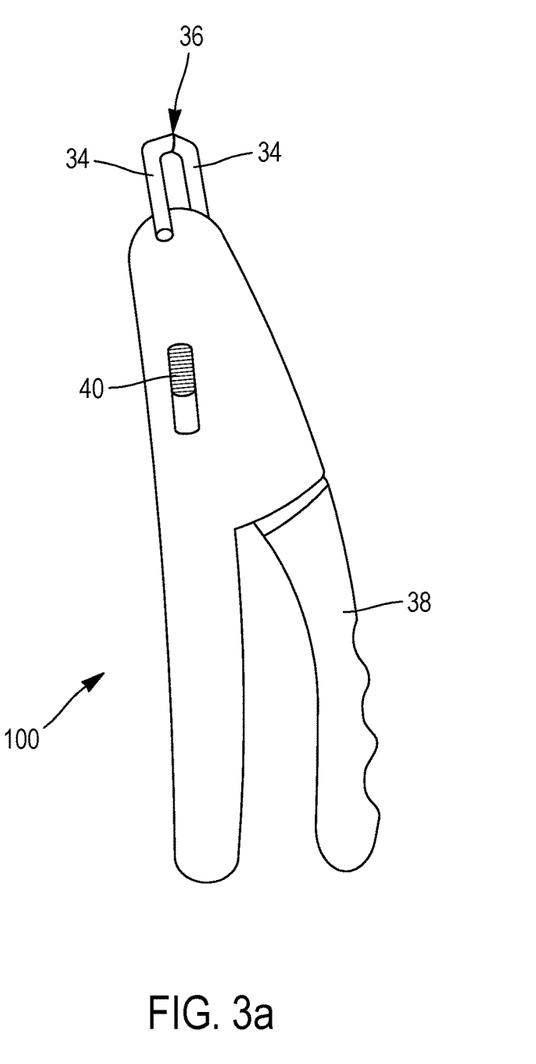
FIG. 3a shows, schematically and in profile, a type of relief device according to the invention which functions by compressing a piezoelectric quartz, the potential of the electrical pulses delivered by the relief device being defined by the compression of the quartz and a switch being configured to put into operation a device for protecting against the static electricity, said protection device being arranged inside the relief device, FIG. 3b schematically shows the relief device from FIG. 3a, seen from the front, the two electrodes in the shape of rods having a round cross-section being placed end-to-end and spaced apart by a few tenths of a millimeter to several millimeters.

Furthermore, the operation of the spark gaps as illustrated in FIGS. 1a to 1e may be carried out by a switch or selector 40 (see FIG. 3a).

When it is put into operation by the switch or selector 40, the spark gap is connected to the electrodes for applying pulses to the skin and makes it possible to generate discharge sparks of the overvoltages which discharge the static electricity from the relief device here. Moreover, this discharge may also be performed via two or more capacitors which form a spark gap by discharging the static electricity according to a predetermined voltage level. In these relief devices which may be of electric or piezoelectric type, a switch or a selector 40 is added to put into operation at least one spark gap as mentioned above, which thus enables several different adjustments by adapting each spark gap to a different sensitivity of a user. For example, a spark gap which defines a spacing of four-tenths of a millimeter limits the emission of discharges to 400 volts and may be put into operation by a switch or selector whereas a spark gap which defines a spacing of eight-tenths of a millimeter will discharge the static electricity at 800 volts. Such a spark gap may, for example, be arranged at the exit of the electrical circuit which leads to the electrodes.

Figure 1E:
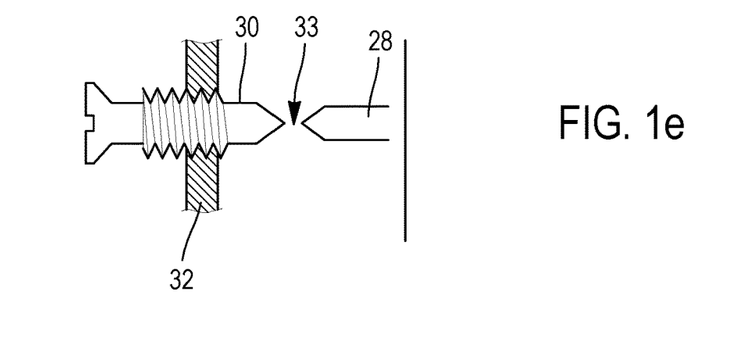

Alternatively, the spacing of the spark gap may be precisely defined by means of a screw made of a conductive material, such as a metal screw which enables an adjustment of the gap of the spark gap for example between two-tenths and ten-tenths of a millimeter between the screw and another conducting element placed end-to-end with the screw. By means of such an adjusting screw, very precise adjustment of the discharge voltage to roughly a tenth of a millimeter, in particular to roughly 100 volts, is permitted. Thus, as shown in FIG. 1e, a fixed point 28 is placed end-to-end with a screw 30 which screws onto a support 32 in order to vary the voltage according to the gap, thus forming the spark gap 33.

This spark gap 33 inside the relief device 100, 200 may be put into operation by turning the screw 30 or even directly from the exterior of the relief device with the aid of a control knob fixed onto the housing, the control knob being able to be turned to, for example, two, three or more positions which are angularly offset from one another. Thus, the adjustment of the gap of the spark gap 33 is carried out in an easily implementable manner particularly by making the screw 30 easily accessible, for example at the battery compartment of the relief device 100, 200. Moreover, a marking may be used on the control knob to define visual tracking of the gap of the spark gap, which makes it possible to know the level of the discharge voltage depending on the rotation of the control knob and to thus adjust the discharge level of the static electricity of the relief device depending on the sensitivity wished by the user.

Alternatively, a series of several spark gaps may be implemented, and in this series the adjustment of the gap for each spark gap may be carried out and a switch or selector makes it possible to choose the adjustment, down to the nearest tenth of a millimeter between two-tenths and ten-tenths of a millimeter, of the gap between the spark gaps to thus enable an adjustment of the discharge voltage, for example from 200 to 1000 volts, by steps of 100 volts.

Figure 2A:
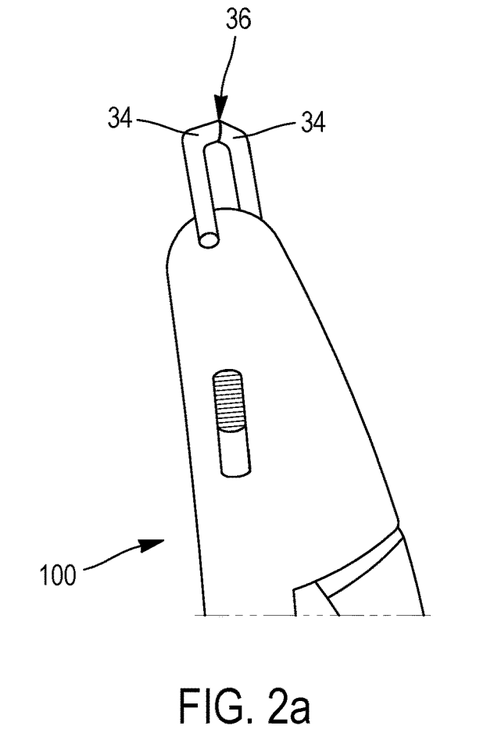
FIGS. 2a, 2b show, schematically, a relief device according to the invention, this device being provided with two electrodes placed end-to-end in order to enable a discharge of static electricity, the relief device being shown in profile in FIG. 2a and from the front in FIG. 2b.
Figure 2B:
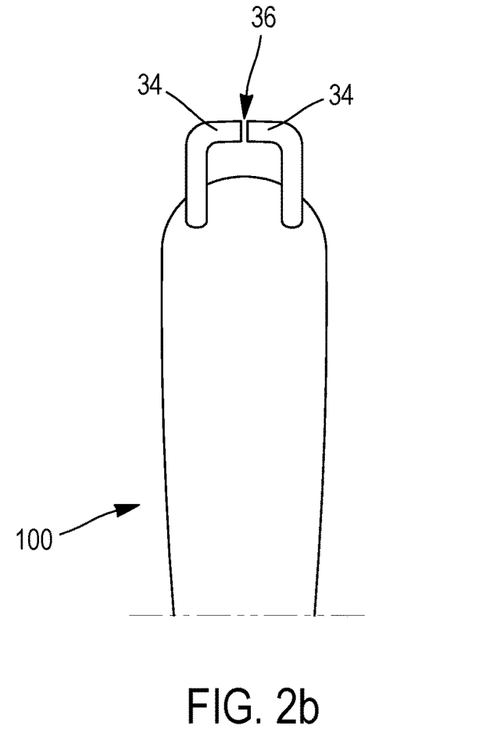
Figure 2C:
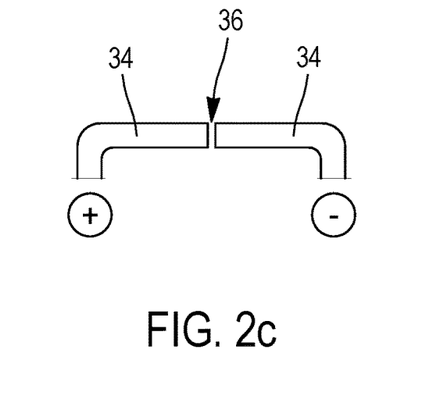
FIG. 2c shows an enlargement of the two electrodes of FIGS. 2a and 2b, these being two electrodes with a round cross-section which are placed end-to-end in order to enable a discharge of static electricity, said electrodes being able to be spaced apart by two-tenths to ten-tenths of a millimeter.

Alternatively, depending on the type of electrodes of the relief device 100, 110, 200, for example for two electrodes created with two rods which have a round cross-section and which are placed end-to-end as illustrated in FIGS. 2a to 2c, the spacing from two-tenths to ten-tenths of a millimeter, which is defined between the electrodes with opposite polarities for the application of electrical stimulations, forms a spark gap and allows protection of the user by limiting the discharge voltage of the relief device's static electricity. Thus, it is the distance between the electrodes which forms a spark gap. In this case, one or more switch(es) or selector (s), each capable of putting at least one spark gap inside the relief device into operation, may be used to allow a discharge of static electricity at lower discharge voltage thresholds compared to the static electricity discharge voltage defined by the spacing between the two electrodes which are placed end-to-end. FIGS. 2a, 2b and 2c illustrate an embodiment example for the electrodes of the relief device that are created with two rods with a round cross-section 34 placed end-to-end and spaced apart by several tenths of a millimeter to several millimeters which act as a spark gap 36. In this case, a switch or a selector makes it possible to choose at least one other spark gap which has a different static electricity discharge voltage for adapting to the most sensitive users.

According to an alternative, the gap between the two electrodes from FIGS. 2a, 2b and 2c is adjustable by means of a screwing-sliding system. According to this alternative, an adjustment of the gap between the housing and at least one of the two electrodes is implemented by means of a screw.

According to another alternative, one type of relief device 100 may comprise a piezoelectric generator which generates an electrical potential intended to supply power to the electrodes by compressing a quartz such as barium titanate, by means of a lever. The voltage between the opposite-polarity terminals of the electrodes is defined depending on a manual pressure applied onto the lever for compressing the quartz. A device for dampening the compression of the quartz, caused by the manual pressure onto the lever, may be implemented for example by means of a spring or a deformable element such as a plastics material to dampen the compression of the quartz by the lever during the application of the manual pressure to thus limit the potential generated at the terminals of the electrodes. In particular, the more or less substantial manual pressure applied by the user onto the lever allows the difference in tension between the terminals of the opposite-polarity electrodes to be adjusted.

Figure 3B:
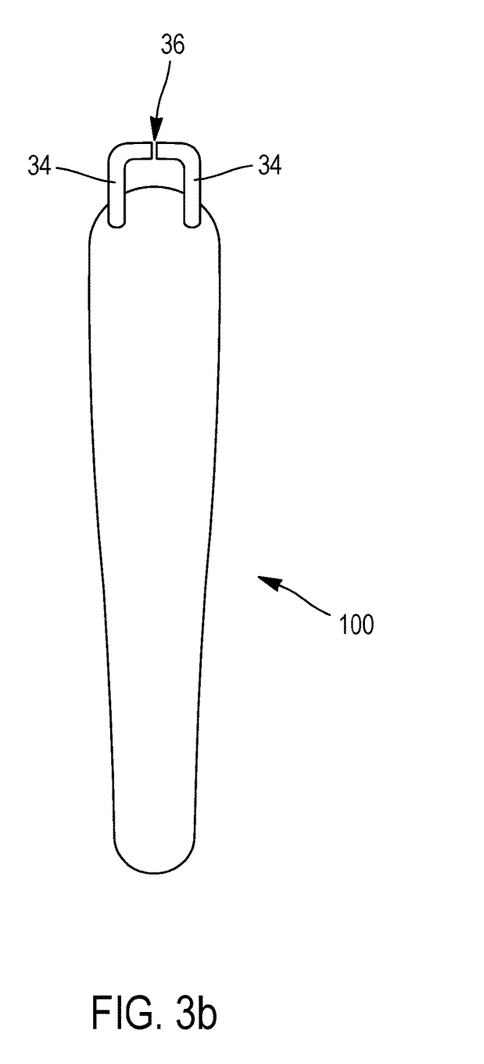

Thus, FIGS. 3a and 3b illustrate an example of a relief device 100 which comprises a piezoelectric quartz with a lever for compressing the piezoelectric quartz to generate, by means of electrodes, potentials intended to be applied onto an area of a user which is to be stimulated.

In FIG. 3a, the difference in tension between the opposite-polarity electrodes placed end-to-end is generated by the compression of the quartz, the difference in tension between the opposite-polarity electrodes being all the greater with the compression of the quartz by the lever.

In FIG. 3b, the spark gap is created by two opposite-polarity electrodes 34 formed by two metal rods having a round cross-section which are spaced apart by six-tenths of a millimeter, which makes it possible to obtain a limitation of the static electricity discharge voltage at 600 volts. This spacing may furthermore be adjustable, for example by means of a screw system (not shown).

In FIG. 3b, there is added in this same relief device 100 a switch 40 which puts into operation a second spark gap 14, 18, 22, 26, 33, situated inside the relief device, the second spark gap defines a spacing of four-tenths, which corresponds to limiting the discharge of static electricity to 400 volts. Thus, the second spark gap makes it possible to reduce by 200 volts the static electricity discharge voltage created by the distance of 0.6 mm between the two electrodes, and thus permits a gentler adjustment for the sensitive users.

Preferably, the limitation of the discharge voltage of the static electricity by two spark gaps is created by two different spark gaps: one spark gap formed by a spacing of one millimeter for the electrodes formed by two metal rods which have a round cross-section and which are of opposite polarity and the installation of an internal spark gap having a lower voltage (by a smaller spacing) with a screw which is adjustable with the aid of a control knob placed outside of the relief device and which allows progressive adjustment by steps of one-tenth to two-tenths of a millimeter to reduce the discharge voltage of the static electricity depending on the choice decided by the user.

Thus, also preferably, when the relief device 100 comprises a piezoelectric quartz, said relief device 100 also comprises a lower-voltage spark gap put into operation by a switch or selector.

Figure 3C:
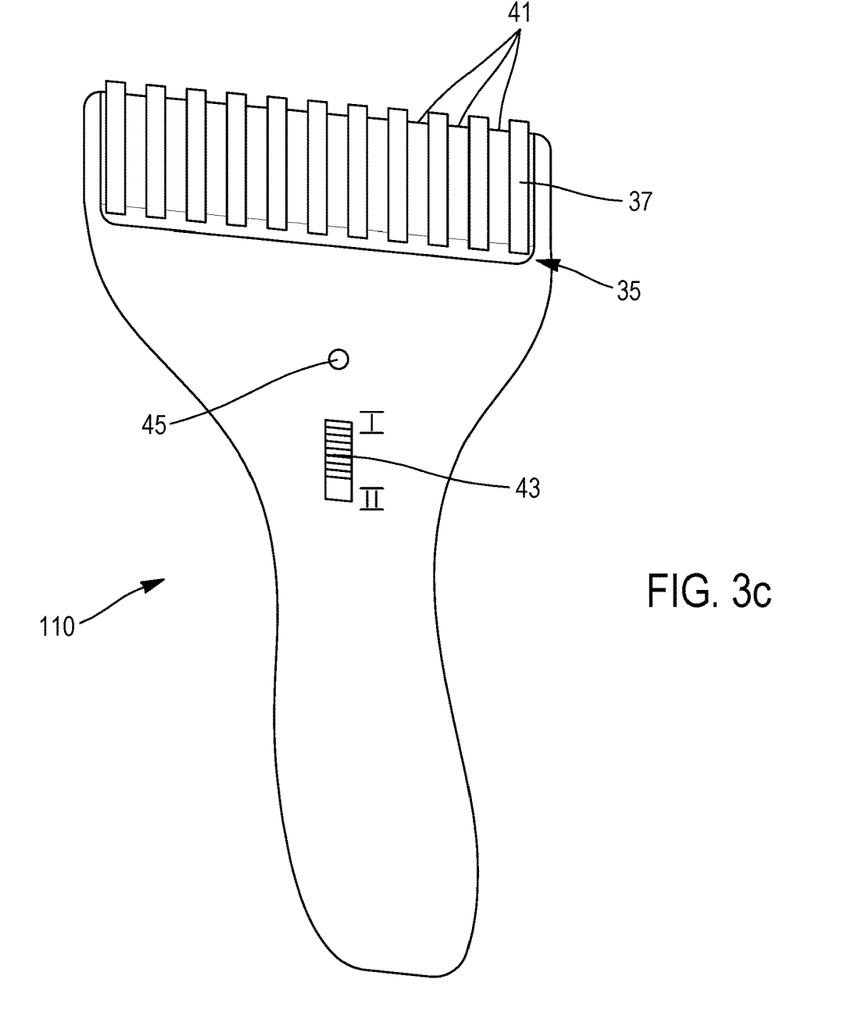
FIG. 3c shows, schematically and from the front, another relief device according to the invention which functions with a piezoelectric quartz, FIG. 3d schematically shows a cross-sectional view of the piezoelectric generator according to FIG. 3c which cooperates with electrodes disposed in an elliptical cross-section cylindrical space delimited by neutral-polarity washers.
Figure 3D:
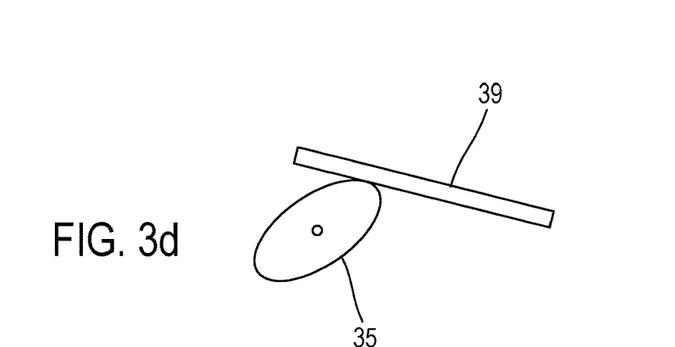

Also preferably, as illustrated in FIG. 3c, a relief device 110 which comprises a piezoelectric material such as a piezoelectric quartz as a piezoelectric generator comprises electrodes 41 arranged in a cylindrical space (for example with an elliptical or circular cross-section) delimited by the neutral-polarity washers 37. As depicted in FIG. 3d, the electrode roll 35 thus formed is cylindrical with an elliptical or circular cross-section and defines a contact with an axle of the piezoelectric generator 39 to generate an electrical potential according to the compression of the axle of the piezoelectric generator 39, said compression being generated by the rolling of the roll 35 of the electrodes on the user. Thus, as illustrated in FIG. 3d, the piezoelectric generator 39 is strained by the electrode roll 35 to generate, at the terminals of the electrodes, a potential which increases with the increase in the speed and the force of compression of the axle of the piezoelectric generator and a potential which decreases as the speed and force of compression of the axle of the piezoelectric generator decreases. In particular, the potential generated at the terminals of the electrodes will be zero when the force of compression of the axle of the piezoelectric generator 39 is zero or when the roll stops rolling on the user. The elliptical or circular cross-section of the roll in particular makes it possible to obtain a progressive compression of the axle of the piezoelectric generator 39 when the relief device is applied onto the user at constant speed. This also makes it possible to vary the potential at the terminals of the electrodes, depending on the speed of movement of the electrodes on the user, between a potential of zero when the roll is not moving on the user and a potential which increases as the speed of movement of the electrodes on the user increases (in one direction or the other of the back-and-forth movement of the application of the roller on the user). Thus, such a configuration of electrodes in a roll 35, combined with a piezoelectric generator 39, makes it possible to deliver various levels of potentials to a user depending on the speed of application of the relief device on the user. Thus, by rolling the roll more or less quickly on the user, it is possible to adjust the electrical pulses delivered, all while taking the sensitivity of the user into consideration.

Thus, this relief device 110 compresses the piezoelectric generator 39 to a greater or lesser degree depending on the speed of the electrode roll 35 which moves on the user. This relief device 110 thus makes it possible to generate a progressive potential during the movement of the relief device on the user. In particular, if the movement of the relief device 110 is slowed on the user, the voltage generated will be lower. As will be explained below, this relief device 110 also allows a potential to be generated at the terminals of the opposite-polarity electrodes solely if the roll 35 is rolling on the user. As illustrated in FIG. 3c, the roll 35 of the relief device 110 comprises an alternation of neutral washers 37 protruding beyond its electrodes 41 to a predetermined distance and which make it possible to create a first device for protection against the static electricity. Indeed, due to the protruding part of the neutral electrodes, the path which the current must travel between the electrodes and the skin which acts as ground may be increased to thus impede a discharge of the static electricity from occurring (because static electricity may accumulate at the electrodes during a previous activation of the electrodes).

Moreover, the projecting distance between the neutral washers 37 and the electrodes 41 also makes it possible to define a minimum voltage below which an electric potential may not be transmitted to the user when the relief device is applied onto the user. Thus, this adjustment of distance makes it possible to precisely define the minimum voltage that is intended to be applied to the user.

In particular, the electrodes 41 are positively and negatively polarized and placed alternatingly, by being separated by the neutral washers 37. A switch or selector 43 situated on the relief device 110 makes it possible to additionally reduce the voltage. A light 45 makes it possible to track the operation of the relief device 110. The neutral washers 37 may for example project beyond electrodes 41 to define the discharge voltage, for example by displacing them by a few tenths of a millimeter in the radial direction of the axle bearing the neutral washers to increase the discharge voltage.

Thus, this first embodiment makes it possible to place at least one device for protecting against static electricity discharges inside the relief device.

In particular, the back-and-forth movement of the axle of the piezoelectric generator may be implemented by a connecting rod which has a first longitudinal end and a second longitudinal end opposite the first longitudinal end, and the first longitudinal end of the connecting rod is engaged with at least one washer which has an elliptical cross-section (which thus forms a crank) and which is rotationally fixed to the neutral-polarity washers 37, and the second longitudinal end of the connecting rod is configured to follow a back-and-forth movement for compressing the piezoelectric quartz when the neutral-polarity washers 37 are rotated by being applied onto the user. Moreover, this type of movement could be replaced by any other type of mechanism which forms a connecting rod and a crank, using a crankshaft, for example.

A second embodiment of the invention relates to a triggering device for triggering and controlling the activation of (the energizing of) the electrical circuit by a bearing detection mechanism, in particular a simple independent mechanical switch which is sensitive to bearing: like a contact or a switch using pressure, for example in which blades or one or more rollers come into contact to trigger the activation of the electrical circuit. These mechanisms for triggering activation of the electrical circuit are able to be arranged at the electrode head on the relief device. The bearing detection mechanism is preferably situated in the electrode head, extending the housing of the relief device 200, which may be configured to return into the housing during the contact between the relief device and the user (see FIG. 4a).

Figure 4A:
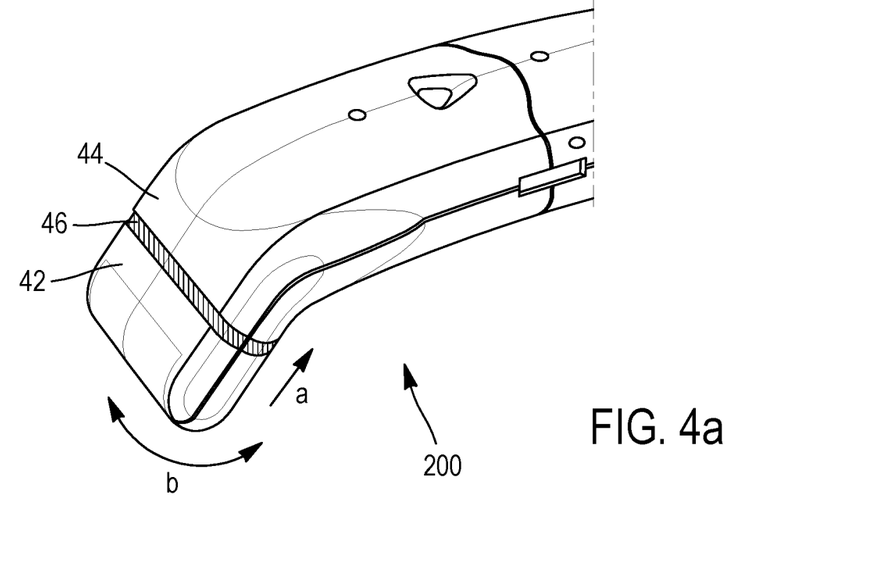
FIG. 4a shows, schematically and in perspective, a relief device according to the invention, the activation of (the energizing of) the electrodes of which is carried out by a switch which triggers their activation via a simple pressure on the electrode head, FIG. 4b schematically shows the relief device from FIG. 4a seen in cross-section, a movement detection is obtained due to an activation contact of the electrical circuit which triggers when the head of the relief device presses onto the body of a user via a return movement of the electrode head into the housing of the relief device.

In FIG. 4a, the activation contact of the electrical circuit is created by a switch which triggers the contact on a simple pressure from the electrode head 42, in the housing 44 of the relief device 200, for example by nesting 46 of the electrode head 42 in the housing 44, in the direction of arrow a, preferably after a latency time triggered by an electronic delayer of a known type of electronic system when a pressure applied onto the electrode head lasts more than half a second and this electronic system preferably triggers a progressive increase in the intensity in the electrical circuit over an additional half-second.

The bearing detection mechanism may also be created by different types of detections such as: a detection via ultrasound echoes, detection via infrared, via ohmmeter, via camera images, via laser reflections, or via any other detector arranged in the electrode head.

Alternatively, the power supply to the electrodes may be triggered with the aid of the electronic system which is configured to generate a progressive intensity in the electrical circuit ranging from a few tenths of a second to several seconds after or in the absence of a latency time at activation, over a few tenths of a second to several seconds.

Alternatively, depending on the type of electrode, there may be provided several contacts with switches in series which trigger the activation when all the electrodes or at least the central electrode is applied onto the user, for example for electrodes created with discs or washers it may be all of the discs or all of the washers or only one central disc or only one central washer. Likewise, when the invention comprises two electrodes created with two rods which have round cross-sections (other cross-sections, such as elliptical, triangular, square, for example, could be implemented) and which are spaced apart (see FIG. 2c), the bearing of the two rods with a round cross-section together against the user may make it possible to trigger the contacting of two switches placed in series to activate the electrical circuit.

Preferably, the contact is created by a switch which activates upon simple pressure on the entirety of the head of the electrode, preferably after a latency time of half a second of circuit opening and preferably with a progressive increase in the intensity in an additional half of a second.

Thus, the second embodiment makes it possible to implement a triggering device which makes it possible to trigger the activation of (the energizing of) the electrical circuit by a bearing detection mechanism, arranged within the relief device 100, 200, by means of the presence of an electronic system which is configured to make it possible to delay the triggering of the activation and which makes it possible to progressively increase the intensity to generate electrical pulses of progressive voltage for a user.

Figure 4B:
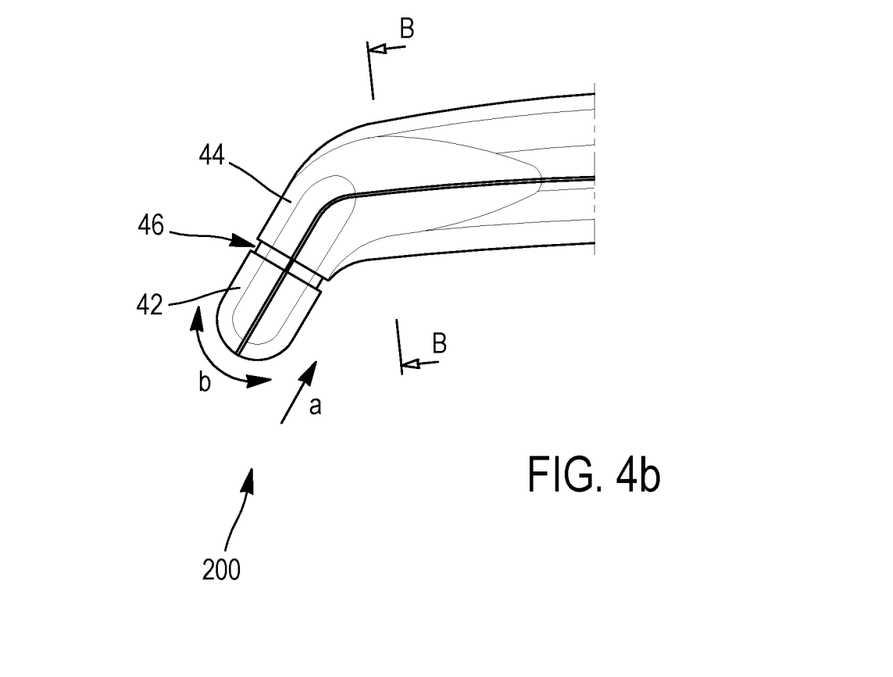

A third embodiment of the invention relates to a triggering device for triggering the activation of (the energizing of) the electrical circuit by a mechanism for detecting the movements of the relief device 100, 200, preferably a back-and-forth movement of the relief device 100, 200, the back-and-forth movement serving to sweep an area to be relieved or an area of use. In FIG. 4b, in a preferred manner, the triggering of the activating contact of the electrical circuit is implemented by contacts which are alternately triggered during the back-and-forth movements of the electrode head 42 in one direction or the other according to arrow b, which are preferably carried out perpendicular to the axis of application of the relief device 200 onto the user. In particular, the contact generated during a change in the direction of the back-and-forth movement of application of the electrodes onto the user generates, by means of the electronic system, the launch of the stimulation after half a second of latency and then the electronic system progressively increases the intensity in the electrical circuit over half a second and maintains the power supply to the electrical circuit as long as the contact is maintained. Thus, it is necessary to make 60 to 80 back-and-forth movements per minute to obtain uninterrupted operation of the stimulations; otherwise, this automatically reduces the intensity with, for example, interruptions in power supply being able to be half a second interrupted by longer or shorter rest times depending on the speed of the back-and-forth movement of the relief device.

Thus, the electrical stimulation may be obtained by rapid back-and-forth movements of the electrode head during the application of the relief device onto a user, by making an activation-triggering contact for the electrical circuit in each direction of the application movement of the relief device on the user, preferably by using a mechanism which makes contact in the two opposing directions of the back-and-forth movement of the application of the relief device on the user.

The triggering of the activation of the electrical circuit may also be obtained by a mechanism outside of the relief device, for example a mechanism configured to roll on the user and which comprises one or more discs or rollers, which rollers are preferably notched or adhesive, which facilitate the adhesion and therefore rolling on the skin without sliding, and which may be made of rubber or another flexible material. Such an outer mechanism may be coupled to a contact which is triggered during a change in the rolling direction of the mechanism on the user.

Figure 5A:
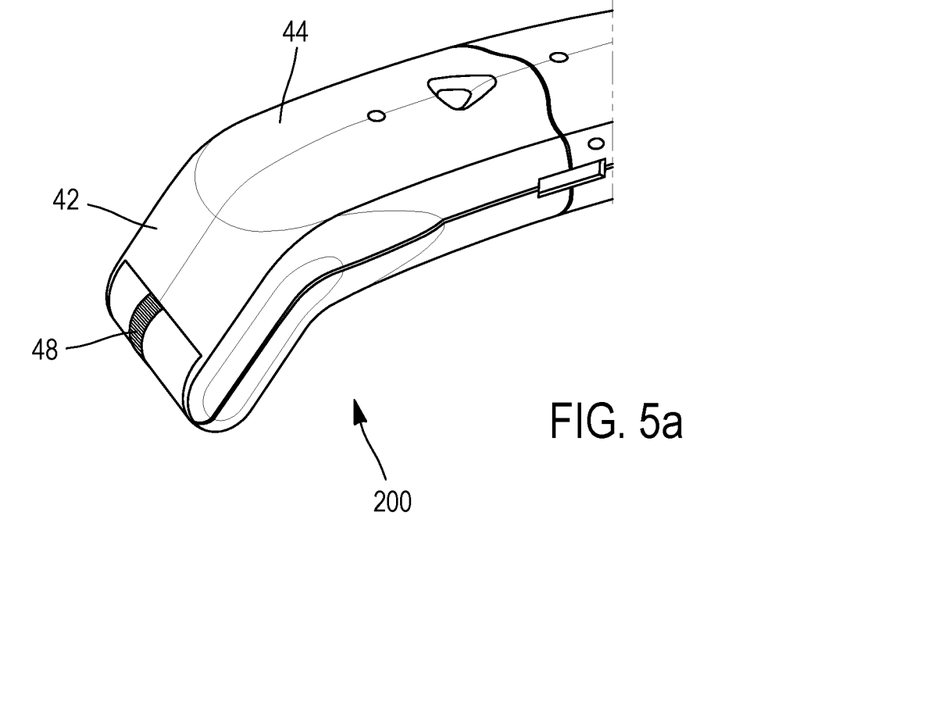
FIG. 5a shows, schematically and in perspective, another embodiment for the activation of the electrical circuit according to the invention which comprises a mechanism for detecting alternating back-and-forth movement, by rolling a roller arranged in the center of the electrode head, FIG. 5b schematically shows the relief device from FIG. 5a viewed in cross-section.
Figure 5B:
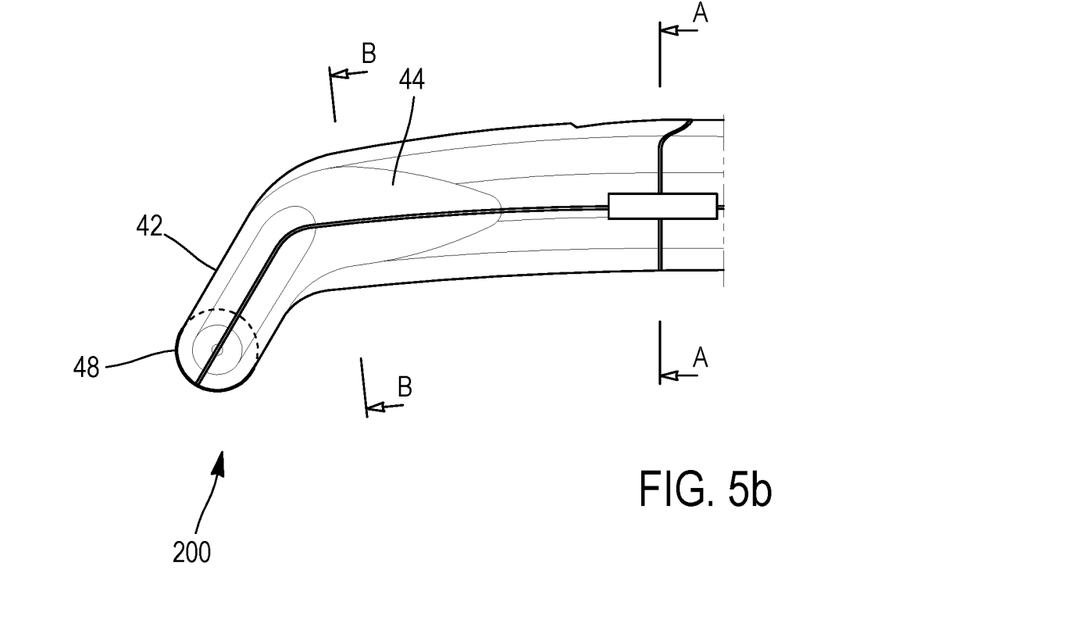
Figure 6A:
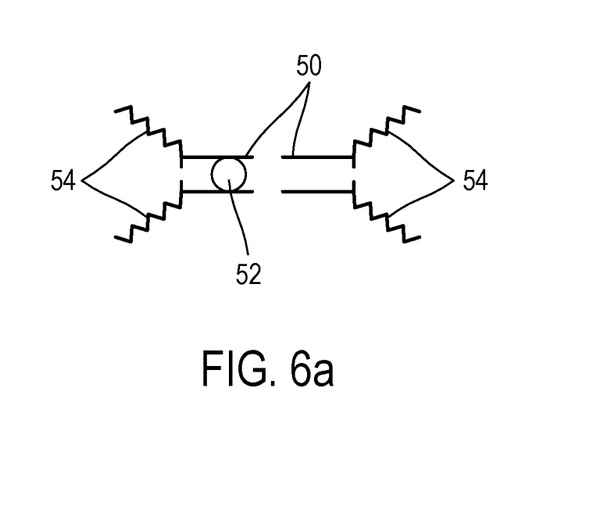
FIGS. 6a to 6c illustrate, schematically, other devices for activating the electrical circuit according to the invention via various movement detection mechanisms.
Figure 6B:
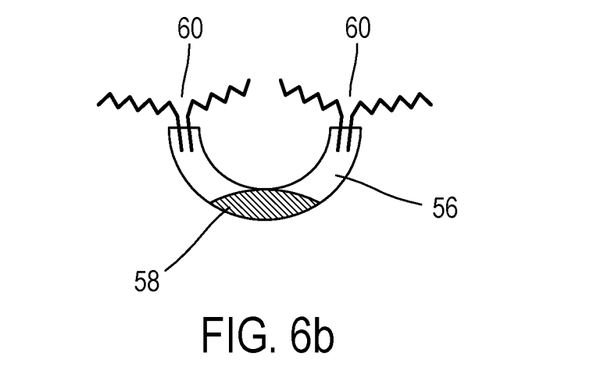

Thus, the electrical stimulation may be obtained by a mechanism inside the relief device situated in the relief device which makes it possible to activate the electrodes in a controlled manner by an electronic system in order to make it possible to activate the electrodes only during the movement of the relief device on the skin in a back-and-forth movement. In particular, to trigger the activation of the electrical circuit, it is possible to use two cylinders and a bead that rolls to establish a contact between the two cylinders in a spacing area between the two cylinders (FIG. 6a) or a metal cylindrical balancing weight which makes contact at the two ends of a pendulum movement (FIG. 6c), or mercury arranged in a curved tube which may move in the tube to make contact in the electrical circuit at the ends of the tube (FIG. 6b). The electronic system may also be used to define a latency time before activation by means of the electronic delayer, which controls a progressive increase in the intensity in the electrical circuit. FIG. 5 illustrates an example of a relief device 200 which comprises a system for triggering the activation of (the energizing of) the electrical circuit via a mechanism for detecting alternating back-and-forth movements, in the direction of application of the relief device on the user. The triggering system of the relief device 200 is controlled by the rolling of a roller 48 arranged in the center of the electrodes 42. The roller rolls on the user and triggers a contact in the two directions of the movement. This roller is arranged in the relief device to be in contact with the user during the application of the electrodes on the user. For example, the roller may be a dynamo which, when it rolls on a user, triggers the activation of the electrical circuit by means of the electronic system which detects a generation of an electrical current by the dynamo and triggers the activation of the electrical circuit as a result.

The electronic system coupled to the alternating contacts of the back-and-forth movement or to the electrical currents triggered by the dynamo is as follows: it deals with the triggering of an electronic time-lag of a few tenths of a second to one second of stimulation which obliges the user to make a minimum of back-and-forth movement per minute to obtain constant electrical pulses, which better distributes the sweep of cutaneous stimulations. A lower rhythm of back-and-forth movement reduces the electrical pulses from a fraction of a second to one second interrupted by longer or shorter rest times depending on the speed of the back-and-forth movement. Thus, for a contact delayed preferably by half of a second, it is necessary to make 60 to 80 back-and-forth movements per minute to obtain electrical stimulations uninterruptedly.

Other alternatives will make it possible to bring about a detection of the retraction movement of the electrode head of the relief device during the application of the relief device onto the user, for example, by using known means such as a laser sensor, an ultrasound wave senor, an image-detection camera or any other means capable of detecting the position of the retractable electrode head within the relief device.

Alternatively, the electronic system for activating and maintaining the activation of the electrical circuit may be created in order to be able to increase or decrease the intensity depending on the frequency of the alternating contacts or of the currents generated by the roller which constitutes a dynamo during the back-and-forth movement of the relief device on the user. The preferred solution is to increase the intensity with the frequency of the back-and-forth movement. This system may thus make it possible to eliminate any necessity to adjust intensity by supplementary rheostat in the relief device.

Figure 6C:
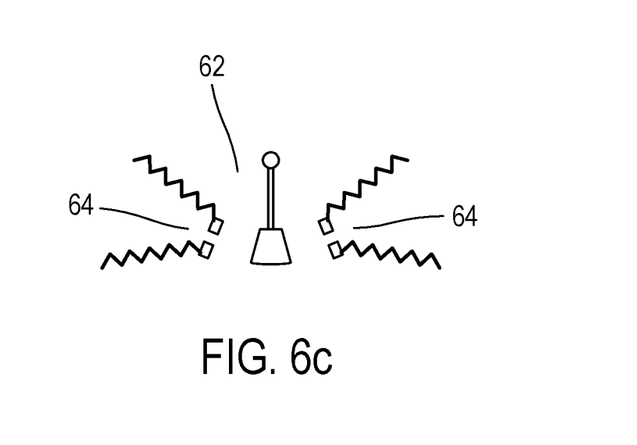

Preferably, the movement is detection by a mechanism for detecting movement of the relief device, when the application head of the electrodes retracts with movements from a few millimeters to a few centimeters which trigger a contact in the electrical circuit of the relief device when the relief device is placed into contact with the user. The alternating contact in each direction of the movement generates, via the electronic system, the launch of a stimulation of half of a second after a first half-second of latency, and then progressively increases the intensity of the power supply current of the electrodes in the following half-second and continues as long as the frequency of the contact associated with the alternating movement is kept at one second, i.e. at a minimum pace of around 60 to 80 back-and-forth movements per minute to obtain constant electric pulses. The electronic system may also be configured to increase the intensity of the power supply current of the electrodes depending on the frequency of the alternating back-and-forth movement. FIGS. 6a, 6b and 6c illustrate devices for activating the electrical circuit via a mechanism for detecting movement of the relief device 200, preferably a back-and-forth movement of the relief device on a user, via a mechanism situated inside the relief device 200, equipped with an electronic activation which occurs only during the movement of the relief device 200 on a user.

Thus, FIG. 6a shows two cylinders 50 between which there rolls a metal bead 52 which places the two cylinders in contact at two ends, of the cylinders, which are placed end-to-end.

FIG. 6b shows a curved cylinder tube 56 in which mercury 58 is arranged, the mercury making it possible to establish an electrical contact in the electrical circuit when it moves at each of the ends of the cylinder.

FIG. 6c shows a pendulum system 62 which makes it possible to establish a contact 64 of the electrical circuit at the two ends of the movement of the pendulum 62.

This activation is coupled to the electronic system which may also adjust a latency time before activation and a progressive increase in the intensity of the electrical circuit and remain activated while the contact associated with the alternating movement is maintained.

The devices for protecting against a discharge of static electricity and for triggering activation of the electrical circuit which supplies power to the electrodes, as these devices are described previously, may be found alone or in combination in the same relief device comprising a piezoelectric quartz or an electrical generator.

Thanks to the above invention, it is possible to obtain the reduction or the elimination of the untimely discharges through static accumulation, when the electrical circuit is activated (is energized) or interrupted, or by stopping the application of the relief device particularly during back-and-forth movements of the relief device on the user. It is also possible to obtain protection against untimely discharges generated by static electricity accumulation by using devices for limiting the discharge of static electricity. Furthermore, it is also possible to use delaying devices and devices for progressively increasing the electrical pulses delivered by the electrodes, by installing one or more of these devices at once, so that they combine for the least painful use possible, specifically adapted to the sensitivity of each individual and thus eliminating any fear of use. These devices will be able to be installed on electrical relief devices which can in particular comprise a piezoelectric material.

Thus, the present invention relates to a relief device 100, 110, 200 for pains and spasms comprising means for protecting a user by limiting the voltage of the static electricity discharges and which makes it possible to trigger the activation of (the energizing of) the electrical circuit which supplies power to the electrodes of said relief device 100, 110, 200. Such a relief device makes it possible to apply electrical pulses which will be better tolerated and less painful by avoiding untimely discharges of static electricity which hamper the use of the relief device 100, 110, 200. The present invention also makes it possible to trigger the operation of said relief device 100, 110, 200 when it is moved, when it bears on a surface of a user, or when it makes a back-and-forth movement on the user. In particular, the relief device 100, 110, 200 comprises several protection means which limit/avoid a discharge of static electricity, and/or one or more means for triggering discharges, and/or an activation delayer, and/or a device for progressively launching the intensity.

The invention claimed is:

1. A relief device for relief of pains and spasms comprising a housing, an electrode head which supports at least two electrodes intended to be applied on an area of use and which is mounted onto the housing, and an electrical circuit for delivering electrical pulses by means of the electrodes, said relief device being characterized in that it comprises:
   a protection device configured to protect a user against static electricity discharges which comprises static electricity discharge elements associated in pairs and adjustably spaced apart from one another, wherein the protection device is configured to discharge static electricity on the at least two electrodes by connecting to the at least two electrodes via a user-controlled switch or actuator, and
   an activation triggering device configured to trigger activation of the electrical circuit only when the relief device bears on the area of use.

2. The relief device according to claim 1, in which the protection device is arranged in the housing and at least two associated static electricity discharge elements are placed end-to-end in the electrical circuit to face one another, and spacing between the two associated static electricity discharge elements being adjustable between 0.2 mm and 1 mm.

3. The relief device according to claim 1, in which the protection device further comprises at least two capacitors arranged in the electrical circuit and configured to discharge static electricity of the relief device at different voltage values.

4. The relief device according to claim 1, in which the protection device further comprises at least two static electricity discharge elements situated outside of the housing and made up of two electrodes, wherein the ends of the two electrodes are placed end-to-end to face one another, the spacing between the ends of the two electrodes being between 0.2 mm and 1 mm.

5. The relief device according to claim 4, in which the spacing between the ends of the two electrodes is adjustable.

6. The relief device according to claim 1, in which the protection device further comprises an adjustment device configured for adjusting a minimum distance between the electrodes and the area of use.

7. The relief device according to claim 6, in which the electrode head comprises neutral-polarity washers, the electrodes and the neutral-polarity washers being disposed in a cylindrical space delimited by the neutral-polarity washers, each neutral-polarity washer being disposed between two adjacent electrodes of opposite polarity, with the neutral-polarity washers projecting beyond the electrodes in a radial direction of the cylindrical space delimited by the neutral-polarity washers.

8. The relief device according to claim 7, in which the activation triggering device is configured to trigger the activation of the electrical circuit when at least one neutral-polarity washer bears on the area of use.

9. The relief device according to claim 8, in which the neutral-polarity washer is arranged in a central part of the cylindrical space.

10. The relief device according to claim 1, in which the activation triggering device is configured to trigger the activation of the electrical circuit when a relative movement occurs between the electrode head and the housing.

11. The relief device according to claim 10, in which the relative movement between the electrode head and the housing is a retraction movement of the electrode head into the housing.

12. The relief device according to claim 1, in which the activation triggering device is configured to trigger the activation of the electrical circuit when at least one roller that is included in the electrode head and that is rotationally fixed to a current-generating dynamo rolls on the area of use.

13. The relief device according to claim 1, in which the activation triggering device is configured to trigger the activation of the electrical circuit when the direction of the application movement of the relief device on the area of use is changed, the application movement being an alternating movement, such as a back-and-forth movement.

14. The relief device according to claim 1, in which the electrical circuit is connected to an activation electronic system configured to delay the activation or progressively increase the potential of the electrical pulses delivered by means of the electrodes.

15. The relief device according to claim 1, in which the electrical circuit is connected to an activation electronic system configured to delay the activation or progressively increase the potential of the electrical pulses delivered by means of the electrodes, for half of a second to one second after the activation triggering device triggers the activation of the electrical circuit.

16. The relief device according to claim 1, in which the electrical circuit is connected to an electronic system for controlling activation that is configured to increase the potential of the electrical pulses delivered by means of the electrodes in accordance with the activation frequency of the activation triggering device.

17. The relief device according to claim 1, including a piezoelectric quartz connected on the one hand to a manually actuated lever and on the other hand to the electrical circuit to deliver the electrical pulses by means of the electrodes, the lever being configured to adjust the potential of the electrical pulses by compression of the lever on the piezoelectric quartz and a dampening device being configured to dampen the compression of the lever on the piezoelectric quartz.

18. The relief device according to claim 7, including a piezoelectric quartz connected on the one hand to a connecting rod which cooperates with at least one washer that has an elliptical cross-section and on the other hand to the electrical circuit to deliver the electrical pulses by means of the electrodes, the connecting rod having a first longitudinal end and a second longitudinal end opposite the first longitudinal end, the first longitudinal end of the connecting rod being engaged with the at least one washer which has an elliptical cross-section and which is rotationally fixed to the neutral-polarity washers, and the second longitudinal end of the connecting rod being configured to follow a back-and-forth movement for compression of the piezoelectric quartz when the neutral-polarity washers are rotated.

19. A relief device for relief of pains and spasms comprising a housing, an electrode head which supports at least two electrodes intended to be applied on an area of use and which is mounted onto the housing, and an electrical circuit for delivering electrical pulses by means of the electrodes, said relief device being characterized in that it comprises:
 a protection device configured to protect a user against static electricity discharges which comprises static electricity discharge elements associated in pairs and adjustably spaced apart from one another, wherein the protection device is configured to discharge static electricity on the at least two electrodes by connecting to the at least two electrodes via a user-controlled switch or actuator, and
 an activation triggering device configured to enable activation of the electrical circuit as a result of the relief device bearing on the area of use.

* * * * *